US012394508B2

(12) United States Patent
Afrasiabi et al.

(10) Patent No.: US 12,394,508 B2
(45) Date of Patent: Aug. 19, 2025

(54) SYSTEMS AND METHODS FOR TRAINING MULTI-ARMED BANDIT MODELS

(71) Applicant: UnitedHealth Group Incorporated, Minnetonka, MN (US)

(72) Inventors: Mohsen Afrasiabi, Madison, WI (US); Tanzeem Choudhury, New York, NY (US); Cecilia M. Livesey, Merion Station, PA (US); Jared Dustin Martin, Minneapolis, MN (US); Herk Anthony Confer, San Francisco, CA (US); Daniel Joseph Mulcahy, Evanston, IL (US); Rony Krell, Brooklyn, NY (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 36 days.

(21) Appl. No.: 18/302,185

(22) Filed: Apr. 18, 2023

(65) Prior Publication Data

US 2024/0145057 A1 May 2, 2024

Related U.S. Application Data

(60) Provisional application No. 63/381,392, filed on Oct. 28, 2022.

(51) Int. Cl.
*G16H 20/00* (2018.01)
*G06N 3/092* (2023.01)

(52) U.S. Cl.
CPC ............ *G16H 20/00* (2018.01); *G06N 3/092* (2023.01)

(58) Field of Classification Search
CPC ........ G16H 20/00; G16H 50/70; G16H 50/20; G06N 20/00; G06N 3/092; G06N 7/01
See application file for complete search history.

(56) References Cited

U.S. PATENT DOCUMENTS

2015/0140527 A1* 5/2015 Gilad-Barach .......... G09B 5/00 434/236
2021/0241873 A1* 8/2021 Kapaldo ............... G16H 50/30
(Continued)

FOREIGN PATENT DOCUMENTS

EP 3859741 A2 8/2021
WO 2022076221 A1 4/2022

OTHER PUBLICATIONS

Zhou et al., "Spoiled for Choice? Personalized Recommendation for Healthcare Decisions: A Multi-Armed Bandit Approach," arXiv: 2009.06108, (Year: 2020).*
(Continued)

*Primary Examiner* — Jonathon A. Szumny
(74) *Attorney, Agent, or Firm* — Bookoff McAndrews, PLLC

(57) ABSTRACT

A method for determining a treatment recommendation using a multi-armed bandit (MAB) model can include receiving first patient information, determining, using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information, and providing the treatment recommendation.

8 Claims, 13 Drawing Sheets

(56) References Cited

U.S. PATENT DOCUMENTS

| | | | | |
|---|---|---|---|---|
| 2022/0013230 A1* | 1/2022 | Wu | G16H 50/50 | |
| 2022/0415472 A1* | 12/2022 | Hakala | G06N 3/092 | |
| 2023/0103124 A1* | 3/2023 | Kano | G16H 50/20 | 705/2 |

OTHER PUBLICATIONS

Cortes, David, “Adapting multi-armed bandits policies to contextual bandits scenarios,” research paper, Nov. 23, 2019, arXiv preprint arXiv:1811.04383, accessible at: https://arxiv.org/pdf/1811.04383.pdf.

Cortes, David, “Contextual Bandits,” website, accessible at: https://github.com/david-cortes/contextualbandits.

* cited by examiner

600

| CASE_ID (602) | BMI (604) | PHQ (606) | MIN_ACTIVITY (608) | IS_MEDICATED (610) | TREATMENT RECOMMENDATION (612) | RESULT (614) |
|---|---|---|---|---|---|---|
| 1 | 30 | 11 | 10 | 0 | THERAPY | 1 |
| 2 | 25 | 5 | 15 | 0 | SHORT DAILY WALKS | 0 |
| 3 | 22 | 6 | 19 | 0 | MINDFUL BREATHING | 1 |
| 4 | 24 | 15 | 37 | 0 | SHORT DAILY WALKS | 0 |
| 5 | 27 | 19 | 56 | 1 | THERAPY | 1 |
| 6 | 43 | 20 | 10 | 1 | THERAPY | 1 |
| 7 | 23 | 14 | 5 | 1 | MINDFUL BREATHING | 1 |
| 8 | 28 | 16 | 12 | 1 | SHORT DAILY WALKS | 0 |
| 9 | 24 | 7 | 7 | 0 | MINDFUL BREATHING | 0 |

| CASE_ID | TREATMENT | BOOTSTRAP SAMPLE |
|---|---|---|
| 1 | THERAPY | THERAPY_1 |
| 5 | THERAPY | THERAPY_1 |
| 1 | THERAPY | THERAPY_2 |
| 6 | THERAPY | THERAPY_2 |
| 2 | SHORT DAILY WALKS | SDW_1 |
| 8 | SHORT DAILY WALKS | SDW_1 |
| 2 | SHORT DAILY WALKS | SDW_2 |
| 4 | SHORT DAILY WALKS | SDW_2 |
| 3 | MINDFUL BREATHING | MB_1 |
| 7 | MINDFUL BREATHING | MB_1 |
| 3 | MINDFUL BREATHING | MB_2 |
| 9 | MINDFUL BREATHING | MB_2 |

| TREATMENT | INTENSITY | EXPENSE | CLINICAL VALUE |
|---|---|---|---|
| THERAPY | 4 | 5 | 5 |
| MINDFUL BREATHING | 1 | 1 | 4 |
| SHORT DAILY WALKS | 2 | 1 | 3 |

| ID | BMI | PHQ | MIN. ACTIVITY | MEDICATED? |
|---|---|---|---|---|
| 10 | 29 | 13 | 9 | 0 |

| BOOTSTRAP_SAMPLE | SCORE |
|---|---|
| THERAPY_1 | 0.7 |
| THERAPY_2 | 0.5 |
| SHORT DAILY WALKS_1 | 0.3 |
| SHORT DAILY WALKS_2 | 0.4 |
| MINDFUL BREATHING_1 | 0.8 |
| MINDFUL BREATHING_2 | 0.4 |

FIG. 6E

SYSTEMS AND METHODS FOR TRAINING MULTI-ARMED BANDIT MODELS

CROSS-REFERENCE TO RELATED APPLICATION(S)

This patent application claims the benefit of priority to U.S. Provisional Application No. 63/381,392, filed on Oct. 28, 2022, the entirety of which is incorporated herein by reference.

TECHNICAL FIELD

The present disclosure relates to systems and methods for training multi-armed bandit (MAB) models, and for determining recommended treatment options using the trained MAB models.

BACKGROUND

The MAB is a problem in reinforcement learning in which there are multiple options associated with respective probabilities of delivering a reward. A MAB model can select an option to maximize (or improve) an expected return in a particular environment. Training MAB models may require a large amount of training data to permit the MAB model to perform a large number of iterations. Accordingly, training MAB models requires a large amount of training data, requires a large number of iterations, is computationally expensive, and is time-consuming. In a clinical environment, a MAB model may determine a treatment recommendation that is inconsistent with clinical guidelines. Accordingly, the MAB model may be inaccurate, error-prone, or inconsistent.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to some embodiments, a computer-implemented method for determining a treatment recommendation using a multi-armed bandit (MAB) model includes receiving, by one or more processors, first patient information; determining, by the one or more processors and using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information; and providing, by the one or more processors, the treatment recommendation.

According to some embodiments, a device for determining a treatment recommendation using a multi-armed bandit (MAB) model includes memory configured to store instructions; and one or more processors configured to execute the instructions to perform operations comprising: receiving first patient information; determining, using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information; and providing the treatment recommendation.

According to some embodiments, a non-transitory computer-readable medium is configured to store instructions that, when executed by one or more processors for determining a treatment recommendation using a multi-armed bandit (MAB) model, cause the one or more processors to perform operations comprising: receiving first patient information; determining, using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information; and providing the treatment recommendation.

Some embodiments herein provide techniques for training MAB models in a manner that reduces the amount of required training data and iterations. For instance, some embodiments herein can train MAB models using patient information such that the MAB models are configured to initially output treatment recommendations in a manner that more accurately reflects the likelihood of the output treatment recommendation being effective. For example, instead of initializing with a probability distribution that assumes that all treatment options include equal likelihoods, some embodiments herein train the MAB models to initialize with probability distributions that indicate non-equal likelihoods of effectiveness of treatment options and that are more accurate.

Moreover, some embodiments herein provide techniques for training MAB models using treatment recommendations determined using the MAB models and clinical treatment recommendations determined using clinical guidelines. In this way, some embodiments herein improve accuracy of the trained MAB models, reduce the number of iterations required for training MAB models, and reduce the amount of training data required for training MAB models. Thus, the technical field of machine learning, particularly, reinforcement learning, is improved.

Some embodiments herein can use the trained MAB models to determine a treatment recommendation for a patient based on patient information of the patient. By using more accurately trained MAB models, some embodiments herein improve the functionality of computing devices associated with the field of machine learning by permitting the computing devices to more accurately determine treatment recommendations using MAB models. Because the more accurately trained MAB models accurately determine treatment recommendations, they also improve patient safety.

It can be understood that both the foregoing general description and the following detailed description are examples and explanatory only and are not restrictive of the embodiments, as claimed.

BRIEF DESCRIPTION OF THE DRAWINGS

The accompanying drawings, which are incorporated in and constitute a part of this specification, illustrate various example embodiments and together with the description, serve to explain the principles of the disclosed embodiments.

FIGS. 6A-6E are diagrams of example data for training a MAB model using an upper confidence bound technique, in accordance with some embodiments of the present disclosure.

DETAILED DESCRIPTION

As discussed above, training MAB models requires a large amount of training data, requires a large number of iterations, is computationally expensive, and is time-consuming. In a clinical environment, a MAB model may determine a treatment option that is inconsistent with clinical guidelines. Accordingly, the MAB model may be inaccurate, error-prone, or inconsistent.

Some embodiments herein provide techniques for training MAB models in a manner that reduces the amount of required training data and iterations. For instance, some embodiments herein can train MAB models using patient information such that the MAB models are configured to initially output treatment recommendations in a manner that more accurately reflects the likelihood of the output treatment recommendation being effective. For example, instead of initializing with a probability distribution that assumes that all treatment options include equal likelihoods, some embodiments herein train the MAB models to initialize with probability distributions that indicate non-equal likelihoods of effectiveness of treatment options and that are more accurate.

Moreover, some embodiments herein provide techniques for training MAB models using treatment recommendations determined using the MAB models and clinical treatment recommendations determined using clinical guidelines. In this way, some embodiments herein improve accuracy of the trained MAB models, reduce the number of iterations required for training MAB models, and reduce the amount of training data required for training MAB models.

Some embodiments herein can use the trained MAB models to determine a treatment recommendation for a patient based on patient information of the patient. By using more accurately trained MAB models, some embodiments herein improve the technical field of machine learning (e.g., particularly machine learning), improve patient safety, and improve the functionality of computing devices associated with the field of machine learning.

Figure 1:
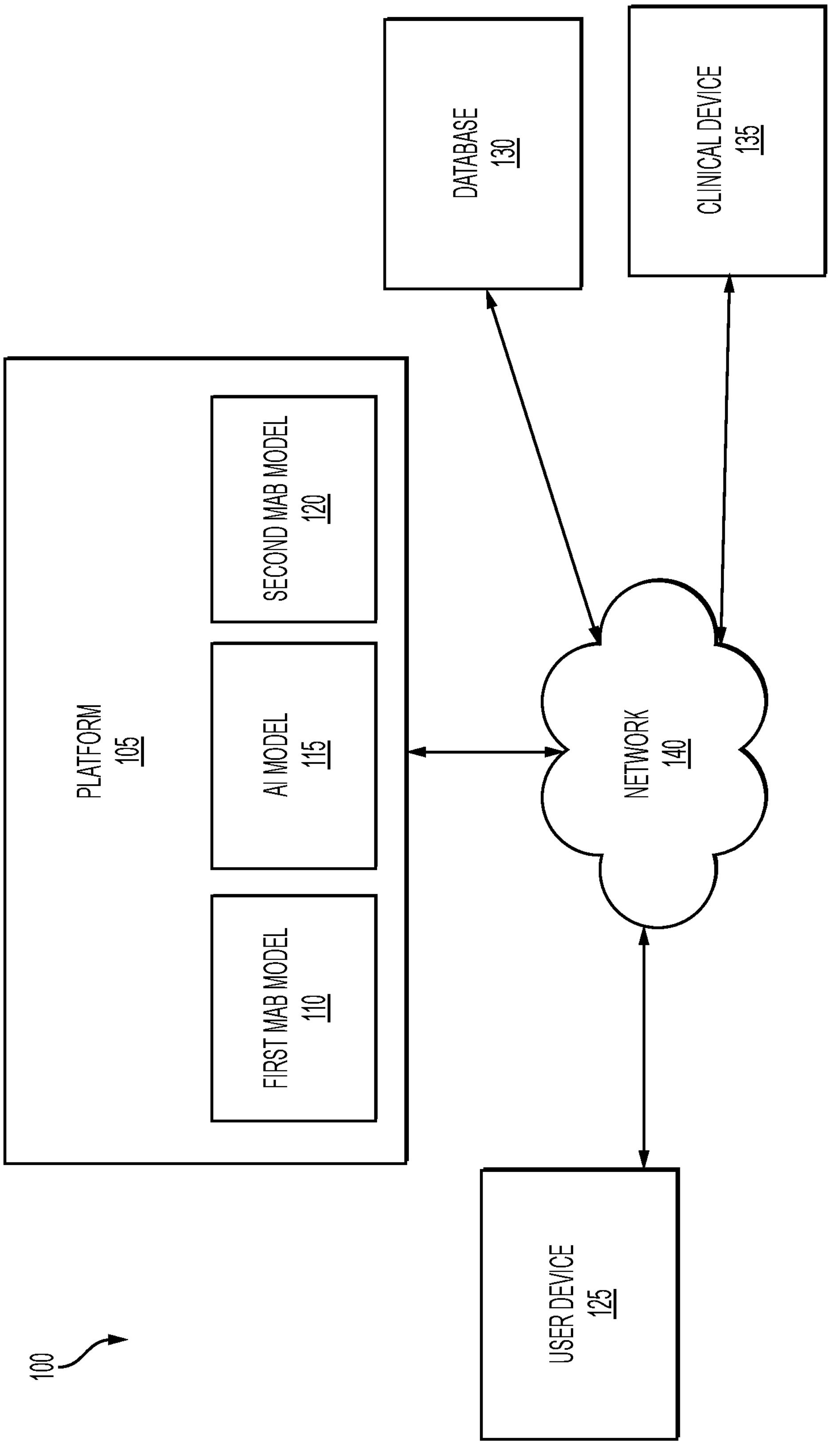
FIG. 1 is a diagram of an example system for training a MAB model, and determining a treatment recommendation using the MAB model, in accordance with some embodiments of the present disclosure.

FIG. 1 is a diagram of an example system 100 for training a MAB model, and determining a treatment recommendation using the MAB model. As shown in FIG. 1, the system 100 can include a platform 105, a first MAB model 110, a second MAB model 120, an artificial intelligence (AI) model 115, a user device 125, a database 130, a clinical device 135, and a network 140.

According to an embodiment, the platform 105 can include a device configured to train the first MAB model 110 and the AI model 115, and use the trained first model 110 and the trained AI model 115 to determine a treatment recommendation based on patient information. According to another embodiment, the platform 105 can include a device configured to train the second MAB model 120, and use the trained second MAB model 120 to determine a treatment recommendation based on patient information. For example, the platform 105 can be a cloud server, a server, a computer, or the like.

The platform 105 can store, or otherwise access, the first MAB model 110, the second MAB model 120, and/or the AI model 115. In some embodiments, the first MAB model 110 can be a model configured to receive patient information, and determine a treatment recommendation based on the patient information using a Thompson sampling technique. In some embodiments, the second MAB model 120 can be a model configured to receive patient information, and determine a treatment recommendation based on the patient information using an upper confidence bound technique. In some embodiments, the AI model 115 can be a model configured to receive patient information, selected treatment information, and selected treatment outcome information, and determine a reward probability distribution of the first MAB model 110. For example, the AI model 115 can be a Bayesian neural network (BNN), a deep neural network (DNN), a logistic regression model, a decision tree model, or the like.

The user device 125 can be a device configured to receive an input of patient information via a graphical user interface, provide the patient information to the platform 105, receive a treatment recommendation from the platform 105, and display the treatment recommendation via the graphical user interface. For example, the user device 125 can be a smartphone, a desktop computer, a laptop computer, a wearable device, or the like.

The database 130 can be a device configured to store training data, patient information, or the like. For example, the database 130 can be a cloud database, a centralized database, a commercial database, a distributed database, or the like.

The clinical device 135 can be a device configured to receive an input of a clinical treatment recommendation determined according to clinical guidelines, and provide the clinical treatment recommendation to the platform 105. For example, the clinical device 135 can be a smartphone, a desktop computer, a laptop computer, a wearable device, or the like.

The network 140 can be a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of the devices of the system 100 shown in FIG. 1 are provided as an example. In practice, the system 100 can include additional devices, fewer devices, different devices, or differently arranged devices than those shown in FIG. 1. Additionally, or alternatively, a set of devices (e.g., one or more devices) of the system 100 can perform one or more functions described as being performed by another set of devices of the system 100. For example, in some embodiments, the user device 125 stores the first MAB model 110, the AI model 115, and/or the second MAB model 120. Alternatively, in some embodiments, the database 130 stores the first MAB model 110, the AI model 115, and/or the second MAB model 120. Alternatively, in yet other embodiments, the first MAB model 110, the AI model 115, and/or the second MAB model 120 are distributed among the platform 105, the user device 125, and the database 130.

Figure 2:
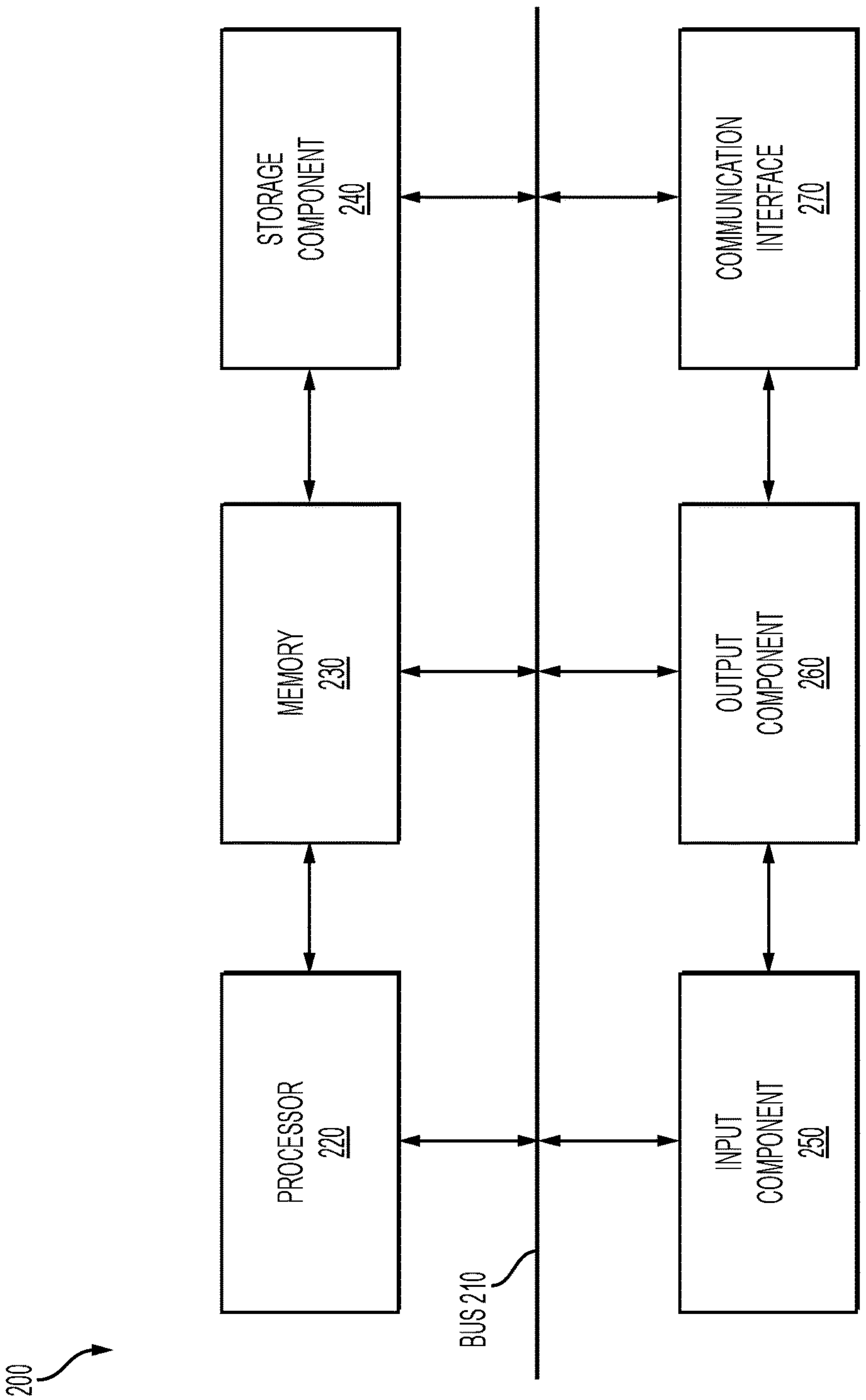
FIG. 2 is a diagram of example components of a device of FIG. 1, in accordance with some embodiments of the present disclosure.

FIG. 2 is a diagram of example components of a device 200. The device 200 can correspond to the platform 105, the user device 125, the database 130, and/or the clinical device 135.

As shown in FIG. 2, the device 200 can include a bus 210, a processor 220, a memory 230, a storage component 240, an input component 250, an output component 260, and a communication interface 270.

The bus 210 includes a component that permits communication among the components of the device 200. The processor 220 can be implemented in hardware, firmware, or a combination of hardware and software. The processor 220 can be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component.

The processor 220 can include one or more processors capable of being programmed to perform a function. The memory 230 can include a random access memory (RAM), a read only memory (ROM), and/or another type of dynamic or static storage device (e.g., a flash memory, a magnetic memory, and/or an optical memory) that stores information and/or instructions for use by the processor 220.

The storage component 240 can store information and/or software related to the operation and use of the device 200. For example, the storage component 240 can include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

The input component 250 can include a component that permits the device 200 to receive information, such as via user input (e.g., a touch screen display, a keyboard, a keypad, a mouse, a button, a switch, and/or a microphone for receiving the reference sound input). Additionally, or alternatively, the input component 250 can include a sensor for sensing information (e.g., a global positioning system (GPS) component, an accelerometer, a gyroscope, and/or an actuator). The output component 260 can include a component that provides output information from the device 200 (e.g., a display, a speaker for outputting sound at the output sound level, and/or one or more light-emitting diodes (LEDs)).

The communication interface 270 can include a transceiver-like component (e.g., a transceiver and/or a separate receiver and transmitter) that enables the device 200 to communicate with other devices, such as via a wired connection, a wireless connection, or a combination of wired and wireless connections. The communication interface 270 can permit the device 200 to receive information from another device and/or provide information to another device. For example, the communication interface 270 can include an Ethernet interface, an optical interface, a coaxial interface, an infrared interface, a radio frequency (RF) interface, a universal serial bus (USB) interface, a Wi-Fi interface, a cellular network interface, or the like.

The device 200 can perform one or more processes described herein. The device 200 can perform these processes based on the processor 220 executing software instructions stored by a non-transitory computer-readable medium, such as the memory 230 and/or the storage component 240. A computer-readable medium can be defined herein as a non-transitory memory device. A memory device can include memory space within a single physical storage device or memory space spread across multiple physical storage devices.

The software instructions can be read into the memory 230 and/or the storage component 240 from another computer-readable medium or from another device via the communication interface 270. When executed, the software instructions stored in the memory 230 and/or the storage component 240 can cause the processor 220 to perform one or more processes described herein. Additionally, or alternatively, hardwired circuitry can be used in place of or in combination with software instructions to perform one or more processes described herein. Thus, implementations described herein are not limited to any specific combination of hardware circuitry and software.

The number and arrangement of the components shown in FIG. 2 are provided as an example. In practice, the device 200 can include additional components, fewer components, different components, or differently arranged components than those shown in FIG. 2. Additionally, or alternatively, a set of components (e.g., one or more components) of the device 200 can perform one or more functions described as being performed by another set of components of the device 200.

Figure 3:
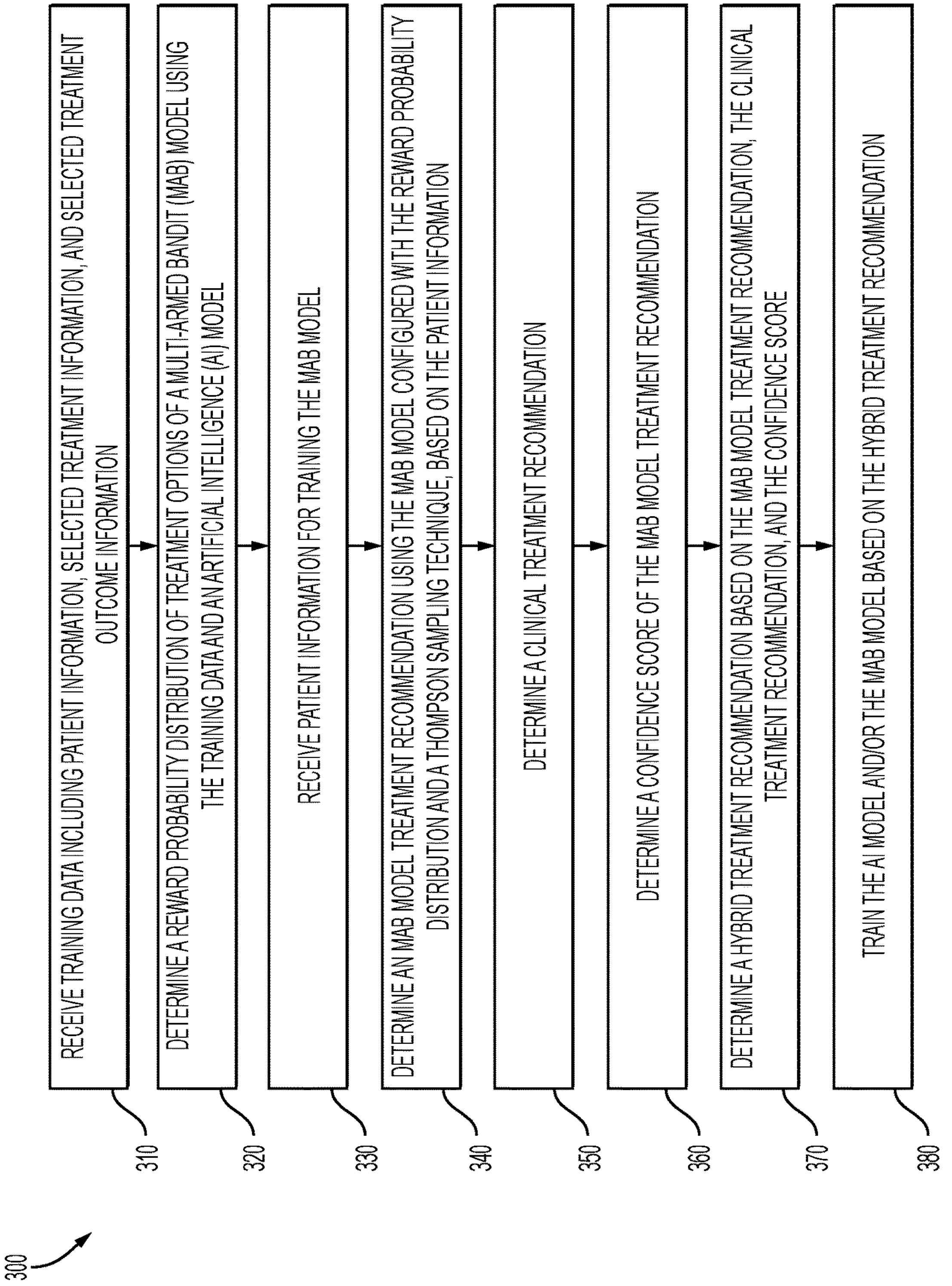
FIG. 3 is a flowchart of an example process for training a MAB model using an AI model and a Thompson sampling technique, in accordance with some embodiments of the present disclosure.

FIG. 3 is a flowchart of an example process 300 for training a MAB model using an AI model and a Thompson sampling technique. Although the process 300 is described herein as being performed by the platform 105 illustrated in FIG. 1, in other embodiments, the process 300 may be performed by the user device 125 or shared by the platform 105 and the user device 125. In some implementations, the platform 105 trains the first MAB model 110 and/or the AI model 115, and provides the trained first MAB model 110 and/or the trained AI model 115 to the user device 125. In this case, the user device 125 stores the trained first MAB model 110 and/or the trained AI model 115 for utilization. Additionally, or alternatively, the platform 105 trains the first MAB model 110 and/or the AI model 115, and provides the trained first MAB model 110 and/or the trained AI model 115 to the database 130. In this case, the database 130 stores the trained first MAB model 110 and/or the trained AI model 115, and provides access to the trained first MAB model 110 and/or the trained AI model 115.

As shown in FIG. 3 at block 310, the process 300 can include receiving training data including patient information, selected treatment information, and selected treatment outcome information. For example, the platform 105 can receive training data including patient information, selected treatment information, and selected treatment outcome information. In some implementations, the platform 105 can receive the training data from the database 130. The training data can be data that is used by the platform 105 to train the AI model 115. The patient information can identify the patient (e.g., a patient identifier, a name, an address, or the like), can identify demographic information of the patient (e.g., age, race, ethnicity, gender, marital status, income, education, employment, or the like), can identify health information of the patient (e.g., height, weight, body mass index, existing conditions, fitness condition, average minutes of daily physical activity, medication information, or the like), can identify symptom information (e.g., symptoms, measurements, indications, or the like), or the like. The selected treatment information can include information identifying a treatment that was selected for the patient based on the patient information. The selected treatment outcome information can include information identifying whether the treatment was effective or non-effective.

Figure 4:
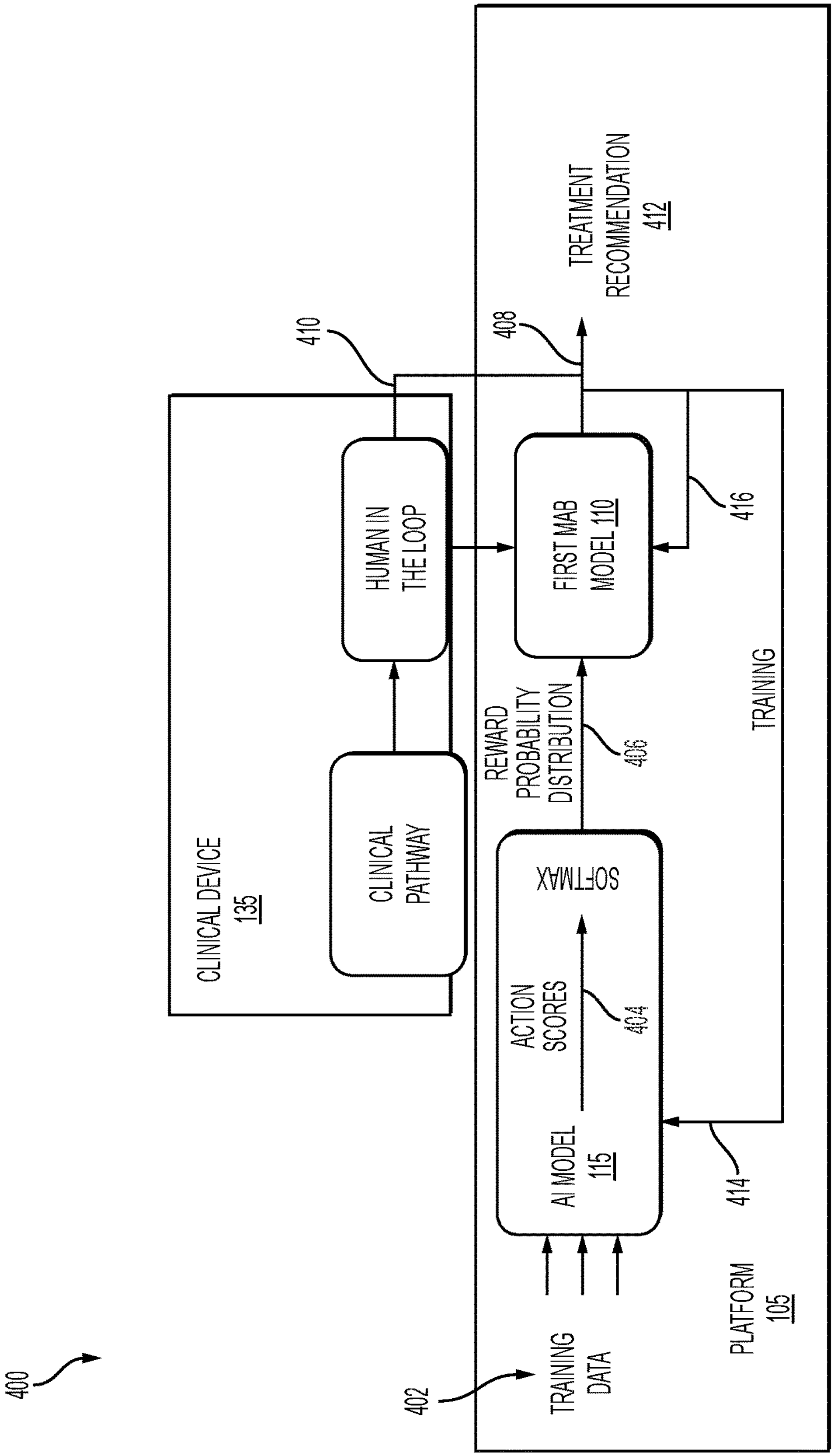
FIG. 4 is a diagram of an example process for training a MAB model using an AI model and a Thompson sampling technique, in accordance with some embodiments of the present disclosure.

As further shown in FIG. 3 at block 320, the process 300 can include determining a reward probability distribution of treatment options of a MAB model using the training data and an AI model. For example, the platform 105 can determine a reward probability distribution of treatment options of the first MAB model 110 using the training data. The first MAB model 110 can be configured to receive patient information as an input, determine a treatment recommendation from among the treatment options, and provide the treatment recommendation as an output. The reward probability distribution can identify respective probabilities of the treatment options being effective for the particular patient information. The platform 105 can input the training data to the AI model 115, and determine the reward probability distribution based on an output of the AI model 115. For example, as shown in FIG. 4, the platform 105 can input 402 the training data into the AI model 115. The AI model 115 can output 404 action scores to a softmax function. The softmax function can output the reward probability distribution. The platform 105 can configure the first MAB model 110 using the reward probability distribution. For example, as shown in FIG. 4, the platform 105 can configure 406 the first MAB model 110 with the reward probability distribution. In this way, the first MAB model 110 can be configured to determine treatment recommendations with an initial reward probability distribution that indicates non-equal likelihoods of effectiveness of treatment options, and that is more accurate than using a reward probability distribution that assumes that all treatment options are equally effective. The platform 105 can determine the reward probability distribution using a variety of supervised learning techniques. Moreover, the platform 105 can update the reward probability distribution using Bayesian estimation methods (e.g., Markov Chain Monte Carlo (MCMC), No U-Turn Sampler (NUTS), or the like), a BNN with end-to-end backpropagation, or the like.

Turning back to FIG. 3, at block 330, the process 300 can include receiving patient information for training the MAB model. For example, the platform 105 can receive patient information. The patient information can identify the patient (e.g., a patient identifier, a name, an address, or the like), can identify demographic information of the patient (e.g., age, race, ethnicity, gender, marital status, income, education, employment, or the like), can identify health information of the patient (e.g., height, weight, body mass index, existing conditions, fitness condition, average minutes of daily physical activity, medication information, or the like), can identify symptom information (e.g., symptoms, measurements, indications, or the like), or the like. In some implementations, the platform 105 can receive the patient information from the user device 105. Alternatively, the platform 105 the platform 105 can receive the patient information based on processing various data, such as electronic health record (EHR) data, claims data, or the like. In this case, the platform 105 can obtain the data from the database 130, can obtain the data based on performing a data retrieval technique, can obtain the data based on an input from another device, or the like.

As further shown in FIG. 3 at block 340, the process 300 can include determining an MAB model treatment recommendation using the MAB model configured with the reward probability distribution and a Thompson sampling technique, based on the received patient information. For example, the platform 105 can determine an MAB model treatment recommendation using the first MAB model 110 configured with the reward probability distribution and a Thompson sampling technique, based on the patient information. For instance, the platform 105 can input the patient information into the first MAB model 110, and determine a MAB model treatment recommendation based on an output of the first MAB model 110. For example, and referring to FIG. 4, the platform 105 can determine 408 a MAB model treatment recommendation based on an output of the first MAB model 110.

Turning back to FIG. 3, at block 350, the process 300 can include determining a clinical treatment recommendation. For example, the platform 105 can receive, from the clinical device 135, the clinical treatment recommendation. To generate the clinical treatment recommendation, the clinical device 135 can receive the same underlying patient information as the first MAB model 110, and display the patient information to an operator (e.g., a physician, a healthcare professional, etc.). The clinical device 135 can receive an input of the clinical treatment recommendation that is determined by the operator based on the patient information and clinical guidelines, and provide the clinical treatment recommendation to the platform 105. For example, and referring to FIG. 4, the platform 105 can determine 410 the clinical treatment recommendation based on information received from the clinical device 135. Clinical guidelines can refer to systematically developed statements to assist practitioner and patient decisions about appropriate treatment recommendations for specific clinical circumstances.

Turning back to FIG. 3, at block 360, the process 300 can include determining a confidence score of the MAB model treatment recommendation determined at block 340. For example, the platform 105 can determine a confidence score of the MAB model treatment recommendation. The confidence score can be a measure of a likelihood that the MAB model treatment recommendation is effective, accurate, or the like. For example, the confidence score can be a confidence interval, a confidence bound, a p-value, or the like. The platform 105 can determine the confidence score based on the number of iterations of the platform 105 determining a MAB model treatment recommendation based on an output of the first MAB model 110. For example, the confidence score can skew towards the MAB model treatment recommendation being effective, accurate, etc., with additional iterations of training.

As further shown in FIG. 3 at block 370, the process 300 can include determining a hybrid treatment recommendation based on the MAB model treatment recommendation, the clinical treatment recommendation, and the confidence score determined at blocks 340, 350, and 360, respectively. For example, the platform 105 can determine a hybrid treatment recommendation based on the MAB model treatment recommendation, the clinical treatment recommendation, and the confidence score. The degree of influence of the MAB model treatment recommendation towards the hybrid treatment recommendation can be based on the confidence score. As an example, and referring to FIG. 4, the platform 105 can determine 412 a hybrid treatment recommendation based on the MAB model treatment recommendation, the clinical treatment recommendation, and the confidence score.

In some implementations, the hybrid treatment recommendation can be a combination of the MAB model treatment recommendation and the clinical treatment recommendation. For example, if the MAB model treatment recommendation is exercise for one hour and the clinical treatment recommendation is exercise for two hours, then the hybrid treatment recommendation can be exercise for one hour and forty five minutes. Alternatively, the hybrid treatment recommendation can be the MAB model treatment recommendation or the clinical treatment recommendation. In the same example above, the hybrid treatment recommendation can be exercise for one hour or exercise for two hours, respectively.

Turning back to FIG. 3, at block 380, the process 300 can include training the AI model and/or the MAB model based on the hybrid treatment recommendation determined at block 370. For example, the platform 105 can train the AI model 115 and the first MAB model 110 based on the hybrid treatment recommendation. In this way, the platform 105 can train the AI model 115 to update the reward probability distribution of the first MAB model 110, and can train the first MAB model 110 to update a reward rate of the first MAB model 110. For example, and referring to FIG. 4, the platform 105 can train 414 the AI model 115, and can train 416 the first MAB model 110 based on the hybrid treatment recommendation. Alternatively, the platform 105 can train the AI model 115 and/or the first MAB model 110 using the MAB model treatment recommendation and/or the clinical treatment recommendation.

The platform 105 can assign a cost to performing iterations of treatment recommendation and reward observation. Further, the platform 105 can assess a cost for performing additional iterations so as to tune parameters to achieve a given confidence threshold in a minimum (or reduced) number of iterations. That is, the platform 105 can iteratively perform operations 330 through 380, and can utilize the cost to reduce a number of iterations required to achieve a particular confidence threshold. In this way, the platform 105 can train the first MAB model 110 in a manner that requires less training data than as compared to situations where a cost is not assessed.

Although FIG. 3 depicts particular blocks and a particular sequence of blocks, it should be understood that the process 300 can include different blocks, differently arranged blocks, or differently ordered blocks.

Figure 5:
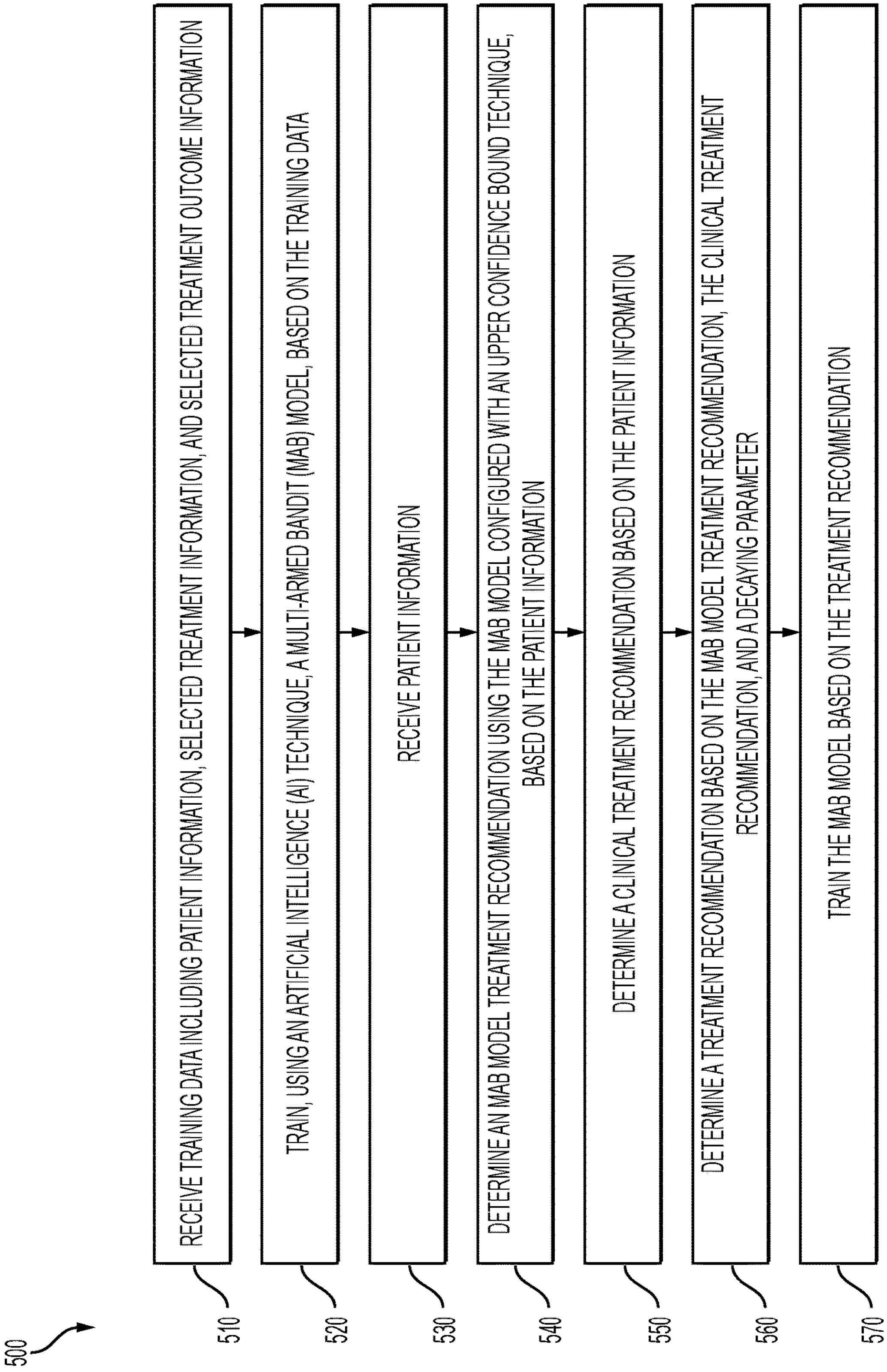
FIG. 5 is a flowchart of an example process for training a MAB model using an upper confidence bound technique, in accordance with some embodiments of the present disclosure.

FIG. 5 is a flowchart of an example process 500 for training a MAB model using an upper confidence bound technique.

As shown in FIG. 5 at block 510, the process 500 can include receiving training data including patient information, selected treatment information, and selected treatment outcome information, similar to block 310 of FIG. 3.

As further shown in FIG. 5 at block 520, the process 500 can include training, using an AI technique, a MAB model, based on the training data. For example, the platform 105 can train the second MAB model 120 using an AI technique. As an example, the platform 105 can encode a collection of rules that reflects existing best practices and clinical pathways for treatment recommendation. For example, if an operator would recommend therapy to a patient with a mild or moderate patient health questionnaire score and who is not medicated, one such rule may encapsulate the aforementioned logic. Another example may be recommending short daily walks to a patient with clinical obesity and a sedentary lifestyle. Further, the platform 105 can, using a bootstrap (e.g., sampling with replacement), create a fixed number (e.g., m) of bootstrap samples per treatment option. In this case, each bootstrap sample can include a fixed number (e.g., x) of datapoints of training data. Each datapoint can include a context vector and an observed reward. The context vector can be a string of numbers representing various pieces of patient information.

For example, and referring to FIG. 6A, the platform 105 can generate data 600 that includes a case identifier 602, a patient's body mass index 604, a latest patient health questionnaire score 606, average minutes of daily physical activity 608, whether or not the patient is on antidepressants 610, a treatment recommendation 612, and reward information 614. Referring to FIG. 6B, the platform 105 can generate data 616 including a case identifier 618, a treatment 620, and a bootstrap sample 622. Referring to FIG. 6C, the platform 105 can generate data 624 including a treatment 626, an intensity 628, an expense 630, and a clinical value 632. Referring to FIG. 6D, the platform 105 can generate data 634 including an identifier 636, a patient's body mass index 638, latest patient health questionnaire score 640, average minutes of daily physical activity 642, and whether or not the patient is on antidepressants 644. The platform 105 can train the second MAB model 120 using the data 600, the data 616, the data 624, and/or the data 634. The platform 105 can train the second MAB model 120 using an AI technique, such as logistic regression, a supervised learning technique, or the like.

Turning back to FIG. 5, at block 530, the process 500 can include receiving patient information, similar to block 330 of FIG. 3. That is, in some implementations, the platform 105 can receive the patient information from the user device 105. Alternatively, the platform 105 the platform 105 can receive the patient information based on processing various data, such as EHR data, claims data, or the like. In this case, the platform 105 can obtain the data from the database 130, can obtain the data based on performing a data retrieval Based on the patient information, the platform 105 can generate a patient's context vector and a treatment vector for each treatment option. Further, the platform 105 can concatenate the treatment option's context vector to the patient's context vector to generate a final vector. The treatment option context vector can be a string of numbers representing various pieces of information about the treatment option. The platform 105 can obtain the treatment option context vector from a saved dictionary, from the database 130, or the like.

Figure 7:
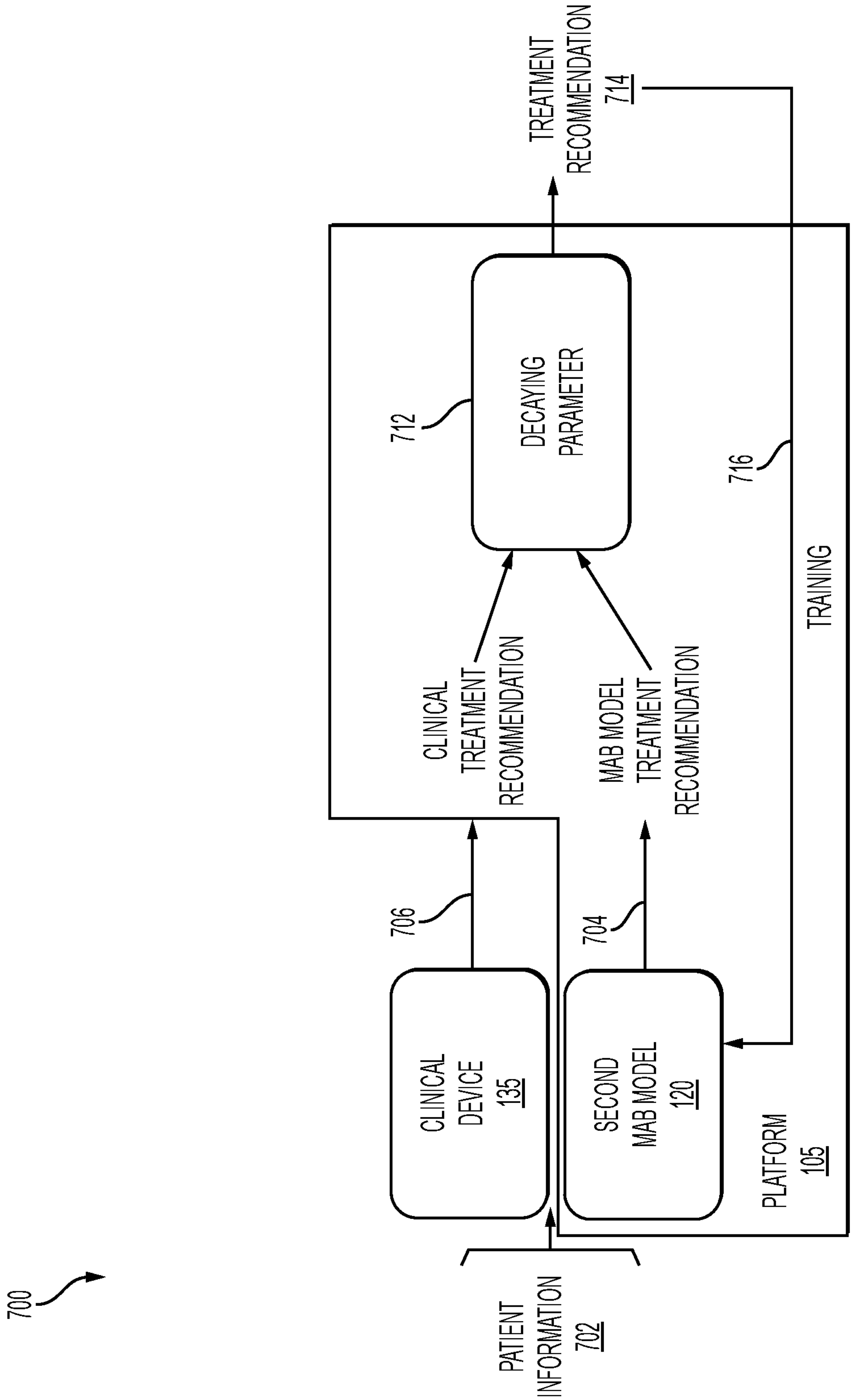
FIG. 7 is a diagram of an example process for training a MAB model using an upper confidence bound technique, in accordance with some embodiments of the present disclosure.

As further shown in FIG. 5 at block 540, the process 500 can include determining an MAB model treatment recommendation using the MAB model configured with an upper confidence bound technique, based on the patient information. For example, the platform 105 can determine an MAB model treatment recommendation using the second MAB model 120 configured with an upper confidence bound technique, based on the patient information. The platform 105 can input the patient information to the second MAB model 120, and determine the MAB model treatment recommendation based on an output of the second MAB model 120. As an example, and referring to FIG. 7, the platform

105 can input 702 the patient information into the second MAB model 120, and determine 704 a MAB model treatment recommendation based on an output of the second MAB model 120.

For example, the platform 105 can run the second MAB model 120 for a treatment on the final vector. The inputs to the second MAB model 120 (e.g., operation 702) can be the concatenated context and treatment vectors. The outputs of the second MAB model 120 (e.g., operation 704) can be a score between zero and one indicating the probability of success that the second MAB model 120 assigns to the treatment. For instance, and referring to FIG. 6E, the platform 105 can determine data including a bootstrap sample identifier 648 and a score 650. The platform 105 can save the result of the $p^{th}$ (e.g., 80%) percentile output. As an example, if the sorted predicted outcomes are [0.53, 0.54, 0.58, 0.61, 0.75], and the platform 105 is configured to use the $80^{th}$ percentile as a proxy for the upper confidence bound, then the platform 105 can select 0.61 as the predicted reward from following this treatment option. In the example shown in FIG. 6E, the platform 105 can choose 0.7, 0.4, and 0.8 for therapy_1, short daily walks_2, and mindful breathing_1, respectively. Further, the platform 105 can select the treatment option with the highest predicted reward as the MAB model treatment recommendation. In the example shown in FIG. 6E, the platform 105 can select mindful breathing_1 (with the score of 0.8) as the MAB model treatment recommendation.

Turning back to FIG. 5, at block 550, the process 500 can include determining a clinical treatment recommendation based on the patient information. For example, the platform 105 can receive, from the clinical device 135, a clinical treatment recommendation determined based on the patient information and clinical guidelines. The clinical device 135 can receive the same underlying patient information as received by the second MAB model 120, and display the patient information to an operator (e.g., a physician, a healthcare professional, etc.). The clinical device 135 can receive an input of a clinical treatment recommendation that is determined by the operator based on the patient information and clinical guidelines, and provide the clinical treatment recommendation to the platform 105. As an example, and referring to FIG. 7, the platform 105 can determine 706 a clinical treatment recommendation based on information received from the clinical device 135.

As further shown in FIG. 5 at block 560, the process 500 can include determining a treatment recommendation based on the MAB model treatment recommendation, the clinical treatment recommendation, and a decaying parameter. For example, the platform 105 can determine a treatment recommendation based on the MAB model treatment recommendation, the clinical treatment recommendation, and a decaying parameter. As an example, and referring to FIG. 7, the platform 105 can use a decaying parameter 712 to determine 714 a treatment recommendation based on the MAB model treatment recommendation and the clinical treatment recommendation. As a particular example, the platform 105 can select the clinical pathway treatment recommendation with a t percent chance, where t starts at a high value initially and then decays as more data is collected. The platform 105 can be configured with any value for t. For example, t can be 98% to start and then decrease to 2% every 50 iterations. The platform 105 can select the MAB model treatment recommendation an increasing number of times as more data is collected. That is, the decaying parameter is configured to cause the platform 105 to bias towards outputs of the second MAB model 120 with each iteration. In the examples shown in FIGS. 6A-6E, and assuming t has decayed to 0.30, the platform 105 can choose therapy to recommend with 30% chance and mindful breathing with a 70% chance. In this case, the platform 105 can select mindful breathing as the treatment recommendation.

In some implementations, the decaying parameter can be configured to decay linearly using a single input variable (e.g., a number of iterations). Alternatively, the decaying parameter can be configured to decay non-linearly using multiple input variables (e.g., past performance, a "clinical-conservativeness" constant, validation metrics from the second MAB model 120, or the like). In this case, the decaying parameter can be quadratic, a neural network, or the like.

Turning back to FIG. 5, at block 570, the process 500 can include training the MAB model using the treatment recommendation. For example, the platform 105 can train the second MAB model 120 using the treatment recommendation. As an example, and referring to FIG. 7, the platform 105 can train 716 the second MAB model 120 using the treatment recommendation. The platform 105 can assign a cost to performing iterations of treatment recommendation and reward observation. Further, the platform 105 can assess a cost for performing additional iterations so as to tune agent parameters to achieve a given confidence threshold in a minimum (or reduced) number of iterations.

Although FIG. 5 depicts particular blocks and a particular sequence of blocks, it should be understood that the process 500 can include different blocks, differently arranged blocks, or differently ordered blocks.

Figure 8:
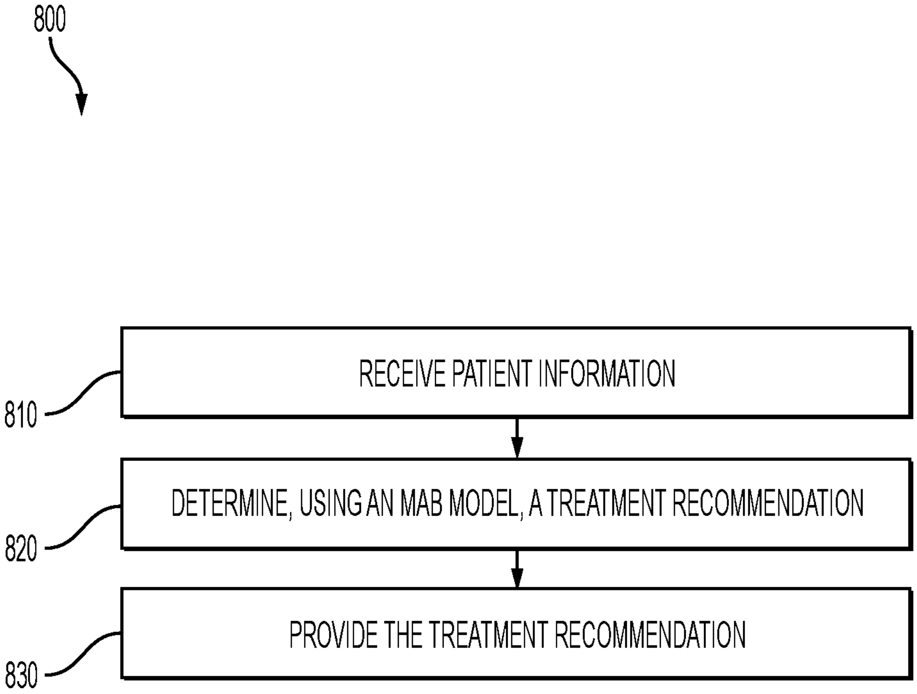
FIG. 8 is a flowchart of an example process for using a MAB model to determine a treatment recommendation, in accordance with some embodiments of the present disclosure.

FIG. 8 is a flowchart of an example process 800 for using a MAB model to determine a treatment recommendation.

As shown in FIG. 8 at block 810, the process 800 can include receiving patient information (e.g., in blocks 330, 530 and operations 402, 702).

Figure 9:
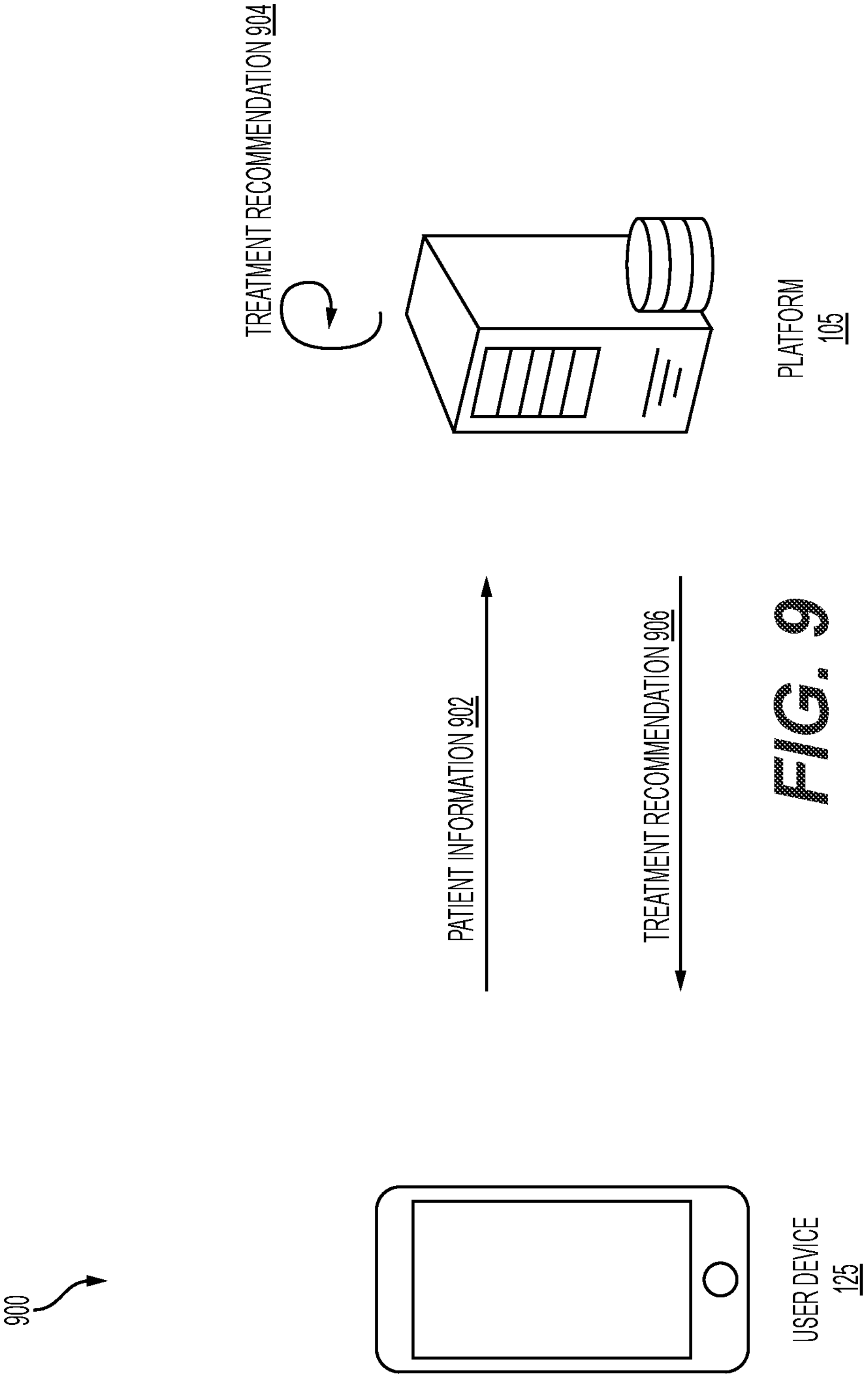
FIG. 9 is a diagram of an example process for using a MAB model to determine a treatment recommendation, in accordance with some embodiments of the present disclosure.

In some implementations, the platform 105 can receive patient information from the user device 125. The user device 125 can display a graphical user interface that permits a patient to input the patient information, receive the patient information via the graphical user interface, and provide the patient information to the platform 105. The patient information can identify the patient (e.g., a patient identifier, a name, an address, or the like), can identify demographic information of the patient (e.g., age, race, ethnicity, gender, marital status, income, education, employment, or the like), can identify health information of the patient (e.g., height, weight, body mass index, existing conditions, fitness condition, average minutes of daily physical activity, medication information, or the like), can identify symptom information (e.g., symptoms, measurements, indications, or the like), or the like. As an example, and referring to FIG. 9, the platform 105 can receive 902 patient information from the user device 125.

Alternatively, the platform 105 can receive the patient information based on processing various data, such as EHR data, claims data, or the like. In this case, the platform 105 can obtain the data from the database 130, can obtain the data based on performing a data retrieval technique, can obtain the data based on an input from another device, or the like.

As further shown in FIG. 8 at block 820, the process 800 can include determining, using an MAB model, a treatment recommendation (e.g., in blocks 370, 560 and operations 412, 714). For example, the platform 105 can determine a treatment recommendation using the first MAB model 110 or the second MAB model 120. As an example, and referring to FIG. 9, the platform 105 can determine 904 a treatment recommendation.

As further shown in FIG. 8 at block 830, the process 800 can include providing the treatment recommendation. For example, the platform 105 can provide, to the user device 125, the treatment recommendation to cause the user device 125 to display the treatment recommendation via the graphical user interface. As an example, and referring to FIG. 9, the platform 105 can provide 906 the treatment recommendation to the user device 125. In this way, the patient can ascertain the treatment recommendation via the graphical user interface of the user device 125.

Some embodiments herein provide techniques for training MAB models in a manner that reduces the amount of required training data and iterations. For instance, some embodiments herein can train MAB models using patient information such that the MAB models are configured to initially output treatment recommendations in a manner that more accurately reflects the likelihood of the output treatment recommendation being effective. For example, instead of initializing with a probability distribution that assumes that all treatment options include equal likelihoods, some embodiments herein train the MAB models to initialize with probability distributions that indicate non-equal likelihoods of effectiveness of treatment options and that are more accurate.

Moreover, some embodiments herein provide techniques for training MAB models using treatment recommendations determined using the MAB models and clinical treatment recommendations determined using clinical guidelines. In this way, some embodiments herein improve accuracy of the trained MAB models, reduce the number of iterations required for training MAB models, and reduce the amount of training data required for training MAB models.

The embodiments herein can use the trained MAB models to determine a treatment recommendation for a patient based on patient information of the patient. By using more accurately trained MAB models, some embodiments herein improve the technical field of treatment recommendation, improve patient safety, and improve the functionality of computing devices associated with the field of treatment recommendation.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention are practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications are made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

The present disclosure furthermore relates to the following aspects.

Example 1. A computer-implemented method for determining a treatment recommendation using a multi-armed bandit (MAB) model, the method comprising: receiving, by one or more processors, first patient information; determining, by the one or more processors and using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information; and providing, by the one or more processors, the treatment recommendation Example 2. The computer-implemented method of Example 1, wherein the MAB model is configured to use a Thompson sampling technique or an upper confidence bound technique to determine the treatment recommendation.

Example 3. The computer-implemented method of any of the preceding examples, further comprising: receiving, by the one or more processors, training data including third patient information, selected treatment information, and selected treatment outcome information; determining, by the one or more processors, a reward probability distribution of treatment options of the MAB model using the training data and an artificial intelligence (AI) model; receiving, by the one or more processors, the second patient information; determining, by the one or more processors, the MAB treatment recommendation using the MAB model configured with the reward probability distribution and the Thompson sampling technique, based on the second patient information; determining, by the one or more processors, the clinical treatment recommendation based on the second patient information; determining, by the one or more processors, a confidence score of the MAB model treatment recommendation; determining, by the one or more processors, a hybrid treatment recommendation based on the MAB model treatment recommendation, the clinical treatment recommendation, and the confidence score; and training, by the one or more processors, the MAB model based on the hybrid treatment recommendation.

Example 4. The computer-implemented method of any of the preceding examples, further comprising: receiving, by the one or more processors, training data including third patient information, selected treatment information, and selected treatment outcome information; training, by the one or more processors and using an artificial intelligence (AI) technique, the MAB model, based on the training data; receiving, by the one or more processors, the second patient information; determining, by the one or more processors, the MAB model treatment recommendation using the MAB model configured with the upper confidence bound technique, based on the second patient information; determining, by the one or more processors, the clinical treatment recommendation based on the second patient information; determining, by the one or more processors, the treatment recommendation based on the MAB model treatment recommendation, the clinical treatment recommendation, and a decaying parameter; and training, by the one or more processors, the MAB model based on the treatment recommendation.

Example 5. The computer-implemented method of any of the preceding examples, wherein the reward probability distribution indicates non-equal likelihoods of effectiveness of treatment options.

Example 6. The computer-implemented method of any of the preceding examples, wherein the receiving the first patient information comprises receiving the first patient information from a user device based on the first patient information being input via a graphical user interface of the user device.

Example 7. The computer-implemented method of any of the preceding examples, wherein the decaying parameter is configured to cause the one or more processors to bias towards outputs of the MAB model with each iteration.

Example 8. A device for determining a treatment recommendation using a multi-armed bandit (MAB) model, the device comprising: memory configured to store instructions; and one or more processors configured to execute the instructions to perform operations comprising: receiving first patient information; determining, using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information; and providing the treatment recommendation.

Example 9. The device of Example 8, wherein the MAB model is configured to use a Thompson sampling technique or an upper confidence bound technique to determine the treatment recommendation.

Example 10. The device of any of Examples 8-9, wherein the operations further comprise: receiving training data including third patient information, selected treatment information, and selected treatment outcome information; determining a reward probability distribution of treatment options of the MAB model using the training data and an artificial intelligence (AI) model; receiving the second patient information; determining the MAB treatment recommendation using the MAB model configured with the reward probability distribution and the Thompson sampling technique, based on the second patient information; determining the clinical treatment recommendation based on the second patient information; determining a confidence score of the MAB model treatment recommendation; determining a hybrid treatment recommendation based on the MAB model treatment recommendation, the clinical treatment recommendation, and the confidence score; and training the MAB model based on the hybrid treatment recommendation.

Example 11. The device of any of Examples 8-10, wherein the operations further comprise: receiving training data including third patient information, selected treatment information, and selected treatment outcome information; training, using an artificial intelligence (AI) technique, the MAB model, based on the training data; receiving the second patient information; determining the MAB model treatment recommendation using the MAB model configured with the upper confidence bound technique, based on the second patient information; determining the clinical treatment recommendation based on the second patient information; determining the treatment recommendation based on the MAB model treatment recommendation, the clinical treatment recommendation, and a decaying parameter; and training the MAB model based on the treatment recommendation.

Example 12. The device of any of Examples 8-11, wherein the reward probability distribution indicates non-equal likelihoods of effectiveness of treatment options.

Example 13. The device of any of Examples 8-12, wherein the receiving the first patient information comprises receiving the first patient information from a user device based on the first patient information being input via a graphical user interface of the user device.

Example 14. The device of any of Examples 8-13, wherein the decaying parameter is configured to cause the one or more processors to bias towards outputs of the MAB model with each iteration.

Example 15. A non-transitory computer-readable medium configured to store instructions that, when executed by one or more processors for determining a treatment recommendation using a multi-armed bandit (MAB) model, cause the one or more processors to perform operations comprising: receiving first patient information; determining, using the MAB model, the treatment recommendation based on the first patient information, wherein the MAB model is trained based on a MAB treatment recommendation determined by the MAB model using second patient information and a clinical treatment recommendation determined according to clinical guidelines based on the second patient information; and providing the treatment recommendation.

Example 16. The non-transitory computer-readable medium of Example 15, wherein the MAB model is configured to use a Thompson sampling technique or an upper confidence bound technique to determine the treatment recommendation.

Example 17. The non-transitory computer-readable medium of any of Examples 15-16, wherein the operations further comprise: receiving training data including third patient information, selected treatment information, and selected treatment outcome information; determining a reward probability distribution of treatment options of the MAB model using the training data and an artificial intelligence (AI) model; receiving the second patient information; determining the MAB treatment recommendation using the MAB model configured with the reward probability distribution and the Thompson sampling technique, based on the second patient information; determining the clinical treatment recommendation based on the second patient information; determining a confidence score of the MAB model treatment recommendation; determining a hybrid treatment recommendation based on the MAB model treatment recommendation, the clinical treatment recommendation, and the confidence score; and training the MAB model based on the hybrid treatment recommendation.

Example 18. The non-transitory computer-readable medium of any of Examples 15-17, wherein the operations further comprise: receiving training data including third patient information, selected treatment information, and selected treatment outcome information; training, using an artificial intelligence (AI) technique, the MAB model, based on the training data; receiving the second patient information; determining the MAB model treatment recommendation using the MAB model configured with the upper confidence bound technique, based on the second patient information; determining the clinical treatment recommendation based on the second patient information; determining the treatment recommendation based on the MAB model treatment recommendation, the clinical treatment recommendation, and a decaying parameter; and training the MAB model based on the treatment recommendation.

Example 19. The non-transitory computer-readable medium of any of Examples 15-18, wherein the reward probability distribution indicates non-equal likelihoods of effectiveness of treatment options.

Example 20. The non-transitory computer-readable medium of any of Examples 15-19, wherein the decaying parameter is configured to cause the one or more processors to bias towards outputs of the MAB model with each iteration.

We claim:

1. A computer-implemented method for determining a treatment recommendation using a multi-armed bandit (MAB) model, the method comprising:

receiving, by one or more processors, first patient information;

determining, by the one or more processors and using the MAB model, the treatment recommendation based on the first patient information, wherein the MAB model is trained based on a MAB model treatment recommendation determined by the MAB model using second patient information and a clinical treatment recommendation determined according to clinical guidelines based on the second patient information; and providing, by the one or more processors, the treatment recommendation, wherein the MAB model is trained by:

receiving training data including third patient information, selected treatment information, and selected treatment outcome information;

determining a reward probability distribution of treatment options of the MAB model using the training data and an artificial intelligence (AI) model;

receiving the second patient information;

determining the MAB model treatment recommendation using the MAB model configured with the reward probability distribution and a Thompson sampling technique, based on the second patient information;

determining the clinical treatment recommendation based on the second patient information;

determining a confidence score of the MAB model treatment recommendation;

determining a hybrid treatment recommendation based on the MAB model treatment recommendation, the clinical treatment recommendation, and the confidence score; and training the MAB model based on the hybrid treatment recommendation.

2. The computer-implemented method of claim 1, wherein the reward probability distribution indicates non-equal likelihoods of effectiveness of treatment options.

3. The computer-implemented method of claim 1, wherein the receiving the first patient information comprises receiving the first patient information from a user device based on the first patient information being input via a graphical user interface of the user device.

4. A system for determining a treatment recommendation using a multi-armed bandit (MAB) model, the system comprising:

one or more non-transitory computer readable media storing processor-executable instructions; and one or more processors configured to execute the processor-executable instructions to perform operations comprising:

receiving first patient information;

determining, using the MAB model, the treatment recommendation based on the first patient information, wherein the MAB model is trained based on a MAB model treatment recommendation determined by the MAB model using second patient information and a clinical treatment recommendation determined according to clinical guidelines based on the second patient information; and providing the treatment recommendation, wherein the MAB model is trained by:

receiving training data including third patient information, selected treatment information, and selected treatment outcome information;

determining a reward probability distribution of treatment options of the MAB model using the training data and an artificial intelligence (AI) model;

receiving the second patient information;

determining the MAB model treatment recommendation using the MAB model configured with the reward probability distribution and a Thompson sampling technique, based on the second patient information;

determining the clinical treatment recommendation based on the second patient information;

determining a confidence score of the MAB model treatment recommendation;

determining a hybrid treatment recommendation based on the MAB model treatment recommendation, the clinical treatment recommendation, and the confidence score; and training the MAB model based on the hybrid treatment recommendation.

5. The system of claim 4, wherein the reward probability distribution indicates non-equal likelihoods of effectiveness of treatment options.

6. The system of claim 4, wherein the receiving the first patient information comprises receiving the first patient information from a user device based on the first patient information being input via a graphical user interface of the user device.

7. One or more non-transitory computer-readable media storing processor-executable instructions that, when executed by one or more processors for determining a treatment recommendation using a multi-armed bandit (MAB) model, cause the one or more processors to perform operations comprising:

receiving first patient information;

determining, using the MAB model, the treatment recommendation based on the first patient information, wherein the MAB model is trained based on a MAB model treatment recommendation determined by the MAB model using second patient information and a clinical treatment recommendation determined according to clinical guidelines based on the second patient information; and providing the treatment recommendation, wherein the MAB model is trained by:

receiving training data including third patient information, selected treatment information, and selected treatment outcome information;

determining a reward probability distribution of treatment options of the MAB model using the training data and an artificial intelligence (AI) model;

receiving the second patient information;

determining the MAB model treatment recommendation using the MAB model configured with the reward probability distribution and a Thompson sampling technique, based on the second patient information;

determining the clinical treatment recommendation based on the second patient information;

determining a confidence score of the MAB model treatment recommendation;

determining a hybrid treatment recommendation based on the MAB model treatment recommendation, the clinical treatment recommendation, and the confidence score; and training the MAB model based on the hybrid treatment recommendation.

8. The one or more non-transitory computer-readable media of claim 7, wherein the reward probability distribution indicates non-equal likelihoods of effectiveness of treatment options.

* * * * *